United States Patent [19]

Brogden et al.

[11] Patent Number: 5,462,735
[45] Date of Patent: Oct. 31, 1995

[54] *PASTEURELLA HAEMOLYTICA* SUBUNIT VACCINE CONTAINING CAPSULAR POLYSACCHARIDE AND MURAMYL DIPEPTIDE

[75] Inventors: Kim A. Brogden, Boone, Iowa; Louis Chedid, Tampa, Fla.

[73] Assignee: The United States of America as represented by the Secretary of Agriculture, Washington, D.C.

[21] Appl. No.: 75,064

[22] Filed: Jun. 10, 1993

[51] Int. Cl.⁶ .......................... A61K 39/102; A61K 39/39
[52] U.S. Cl. ....................................... 424/255.1; 424/279.1
[58] Field of Search ............................... 424/255.1, 279.1

[56] References Cited

U.S. PATENT DOCUMENTS

| | | | |
|---|---|---|---|
| 4,186,194 | 1/1980 | Adam et al. | 424/89 |
| 4,427,659 | 1/1984 | Lefrancier et al. | |
| 4,461,761 | 7/1984 | Lefrancier et al. | |
| 4,803,070 | 2/1989 | Cantrell et al. | 424/88 |
| 4,939,122 | 7/1990 | Phillips et al. | 530/322 |

OTHER PUBLICATIONS

Van De Wijgert et al (1991) Infection and Immunity 59 (8): 2750–2757.
Byars et al (1987) Vaccine 5: 223–228.
Ponpipom et al (1983) *Carbohydrate Res* 113: 45–56.
Ponpipom et al (1983) Carbohydrate Res 113: 57–62.
Kim A. Brogden et al., "Effect of Muramyl Dipeptide on Immunogenicity of *Corynebacterium pseudotuberculosis* Whole–Cell Vaccines in Mice and Lambs," American Journal of Veterinary Research 51(2): 200–202 (Feb. 1990).
C. Adlam et al., "Capsular Polysaccharide Structures of *Pasteurella haemolytica* and Their Potential as Virulence Factors," In Protein–Carbohydrate Interactions in Biological Systems, pp. 391–393 Wellcome Foundation Ltd. (1986).
C. Adlam et al., "Purification, Characterization and Immunological Properties of the Serotype–Specific Capsular Polysaccharide of *P. haemolytica* (Serotype A1) Organisms," Journal of General Microbiology 130: 2415–2426 (1984).

*Primary Examiner*—Kay K. A. Kim
*Attorney, Agent, or Firm*—M. Howard Silverstein; Curtis P. Ribando; John D. Fado

[57] ABSTRACT

Protection of ruminants against bacterial pneumonia caused by *Pasteurella haemolytica* has been achieved with a subunit vaccine. The vaccine contains two principle components; capsular polysaccharide of *P. haemolytica* and a synthetic adjuvant, muramyl dipeptide. This vaccine prevented bacterial infection of the lungs of vaccinated animals upon challenge with *P. haemolygica*. In contrast, animals that were not vaccinated or animals that were vaccinated with only capsular polysaccharide alone had severe lesions and high concentrations of *P. haemolytica* in the lung.

16 Claims, No Drawings

PASTEURELLA HAEMOLYTICA SUBUNIT VACCINE CONTAINING CAPSULAR POLYSACCHARIDE AND MURAMYL DIPEPTIDE

BACKGROUND OF THE INVENTION

1. Field of the Invention This invention relates to protection of ruminants from the effects of stress, particularly those involving an outbreak of virulence of *Pasteurella haemolytica*. *Pasteurella haemolytica* is a gram-negative bacterium that inhabits the upper respiratory tract of ruminants. During periods of stress, the organism enters into a virulent stage and proliferates in the respiratory tract. There, it may be inhaled into the lungs, inducing a disease called pneumonic pasteurellosis or shipping fever of cattle. All U.S. cattle, sheep, and goats are susceptible. There are 16 serotypes of *P. haemolytica* based on chemical differences in the outer capsular polysaccharide. *P. haemolytica* serotype Al is the primary cause of pneumonic pasteurellosis in cattle. The resulting pneumonia is costly to the producer and difficult to treat. Some animals die. In cattle alone, shipping fever accounts for an estimated loss of three billion dollars worldwide of which $500 million dollars is from the United States.

2. Description of Prior Art

Many veterinary products are available that contain *P. haemolytica* but their effectiveness in preventing pneumonic pasteurellosis is questionable. Resistance to experimentally induced pneumonic pasteurellosis can be enhanced by vaccination with live *P. haemolytica*, but not with formalin-killed *P. haemolytica*, *P. haemolytica* leukotoxin or *P. haemolytica* lipopolysaccharide. In fact, it is not uncommon for some animals vaccinated with live vaccines to have complications or animals with formalin-killed vaccines to have more severe lesions than nonvaccinated animals. This applies also to the poorly immunogenic capsular polysaccharide of *P. haemolytica* serotype Al which is composed of N-acetylaminomannuronic acid and N-acetylmannosamine.

SUMMARY OF THE INVENTION

We have unexpectedly discovered that by addition of a muramyl peptide, the capsular polysaccharide of *P. haemolytica*, particularly that of type Al, can be transformed into an effective vaccine capable of providing a protection against stress-induced virulence of *P. haemolygica*. In laboratory trials, vaccines comprising the capsular polysaccharide and adjuvant prevented bacterial infection of the lungs of vaccinated sheep upon challenge with *P. haemolytica*. In contrast, sheep that were not vaccinated or sheep that were vaccinated with only capsular polysaccharide had severe lesions and high concentrations of *P. haemolytica* in the lung.

In accordance with this discovery, it is an object of the invention to prepare a *P. haemolytica* subunit vaccine which is capable of inducing protection; in other words, a high degree of immunity against stress-induced virulence of *P. haemolytica*.

It is also an object of the invention to prepare a *P. haemolytica* subunit vaccine which is safe to handle, incapable of inducing adverse side effects during vaccination, and incapable of inducing the disease in the vaccinated animal.

Another object of the invention is to prepare a *P. haemolytica* subunit which is relatively simple, chemically defined in its constituents, and economically feasible to produce.

Other objects and advantages of the invention will become readily apparent from the ensuing description.

Deposit of Biological Material

The *P. haemolytica* strain P-1075 used herein as a source of capsular polysaccharide was deposited on May 4, 1993, under the conditions of the Budapest Treaty with the American Type Culture Collection, Rockville, Md., and has been assigned Accession Number ATCC 55423.

DESCRIPTION OF THE INVENTION

The term "ruminant" is used throughout the disclosure to include cattle, sheep, goats, and any other cud-chewing animal, wild or domestic, which is susceptible to pneumonic pasteurellosis caused by *P. haemolytica* under stress conditions. Unless otherwise specified, the term *Pasteurella haemolytica* includes all immunogenic types, serologic types, and all strains thereof that may induce disease that is clinically similar to pneumonia caused by what is known as type Al.

"Subunit vaccine" is used throughout the disclosure to mean a type of vaccine comprising distinct chemically defined components (i.e., protective antigens) which are capable, when associated with a muramylpeptide, of inducing protective immunity against stress-induced virulence of *P. haemolytica*.

"Capsular polysaccharide" is used throughout the disclosure to mean a purified bacterial component from *P. haemolytica* comprised of N-acetylaminomannuronic acid and N-acetylmannosamine. Adlam et al. [*Protein-Carbohydrate Interactions in Biological Systems*, pp 391–393 (1986)] reports that the actual structure of the *P. haemolytica* Al capsular polysaccharide is →3)-β-N-acetylaminomannuronic-(1→4)-β-N-acetymannosamine -(1→with the 4 position of the uronic acid being O-acetylated. The *P. haemolytica* capsular polysaccharide for use herein is recovered from the whole organism by any known method, such as the isolation and purification procedure of Adlam et al. [*Journal of General Microbiology* 130:2415–2426 (1984)] described in Example 1.

"Synthetic adjuvant" is used throughout the disclosure in its usual sense to mean a laboratory-synthesized substance that, when added to an antigen, causes the elicitation in vivo of an immunogenic response superior to that imparted by the antigen itself. The synthetic adjuvants contemplated for use in the invention include any of a variety of muramyl dipeptide analogs represented by the general formula:

$$R-CH-CO-X-NH-CH-COR_1$$
with substituents including $CH_2OH$, $O$, $OH$, $HO$, $NH-COCH_3$, $(CH_2)_2$, $COR_2$ Where R is a hydrogen or a methyl group.

X is an amino acid and preferentially L-Ala, L-Leu, L-ILeu, L-Val, L-Ser, L-Thr, L-(N-Methyl) Ala, D-Ala.

R1 is OH, $NH_2$ or $OCnH_{2n+1}$ with n being 1, 2, 3 or 4.

R2 is OH, NH2, $OC_nH_{2n+1}$ (with n being up to 20), sn glyceryl dipalmitoyl or Y-Z.

Where Y is an amino acid, preferentially L-Ala or L-Lys, and Z is OH, $NH_2$, $OC_nH_{2n+1}$ with n being up to 20 or sn glyceryl dipalmitoyl.

A preferred muramyl dipeptide is the N-acetylmuramyl-L-alanyl-D-isoglutamine or its glyceryl dipalmitoyl derivative (N-acetyl-muramyl-L-alanyl-D-isoglutamine, beta, gamma-dipalmitoyl-sn-glycerol) described in the examples, below. Other muramyl dipeptides having the aforementioned properties and contemplated for use herein include the compounds described in the following patents:

French patents BF 7422909 issues Jul. 30, 1979 BF 7529624 issued Sep. 3, 1979

U.S. Pat. Nos. 4,186,194 issued Jan. 29, 1980 4235771 issued Nov. 25, 1980

Canadian patents 1060795 issued Aug. 20, 1979 1060796 issued Aug. 21, 1979 herein incorporated by reference. More precisely, those compounds include Nac-Mur-L-Ala-D-Glu and Nac-Mur-L-Ala-D-isoGln-L-Lys. Also part of the invention are the mono-and diesters of Nac-Mur-L-Ala-D-Glu and the esters of Nac-Mur-L-Ala-D-isoGln.

Another preferred muramyl peptide is Nac-Mur-L-Ala-D-isoGln-sn-glycerol-dipalmitoyl and the compounds described in French patent 8407340 issued Feb. 8, 1988 and its extensions, particularly U.S. Pat. No. 4,939,122 issued Jul. 3, 1990, herein incorporated by reference.

Other muramyl peptides to be part of the invention are Nac-Mur-L-Ala-D-isoGln-L-Ala-2 (1,',2' dipalmitoyl)-sn glycero-3' phosphoryl ethyl amide (MTP-Pe), Nac-glucosaminyl-Nac-Mur-L-Ala-D-isoGln-L-Ala-glyceryl-dipalmitate (DTP-GDP) Nac-Mur-L-Thr-D-isoGln, Nac-Mur-L-Thr-D-isoGln-1,2 dipalmitoyl-sn-glycerol, Nac-Mur-D-Ala-D-isoGln-1,2 dipalmitoyl-sn-glycerol, Nac-Mur-L-Ala-D-Gln and its esters.

The polysaccharide and the muramyl dipeptide are conveniently maintained as separate stock solutions, wherein the agents are suspended in a suitable buffer, such as saline, phosphate buffered saline, Tris-buffered saline, or the like. When formulated into the vaccine, the stock solutions are combined with a pharmaceutically acceptable carrier or vehicle, usually mineral oil or some other oleagenous material. For stabilizing oil-based suspensions, preferred emulsifying agents are monooleates, such as sorbitan monooleate, mannide monooleates, and monooleate emulsifiers sold under the tradenames "Arlacel A" and "Montanide". In selecting an amount of muramyl dipeptide to include in the vaccine, it is important that the level is high enough to produce the desired adjuvant effect, but not so high to have an immunosuppressive effect on the vaccinated animal. The level will of course vary with the type of ruminant being treated and the regimen of administration. A 2O person of ordinary skill in the art would be able to determine the optimum level. The relative amounts of the remaining components are not particularly critical provided that the formulation is stable and contains the desired dose level of vaccine. For the mere purpose of illustration, these relative amounts may be in a weight ratio of the muramylpeptide to the capsular polysaccharide of from about 5:1 to about 1:200, and preferably in the range of about 1:1 to about 1:20. It must of course be understood that such ratios may vary from one muramyl-peptide to another, and from one polysaccharide to another. In a preferred formulation protocol, stock solutions of each of the capsular polysaccharide, muramyl dipeptide, and emulsifying agent are added to the mineral oil and simultaneously emulsified. For small amounts of vaccine (i.e., <50 doses), emulsification can be achieved Typically, each dose of vaccine will comprise from about 10 to about 1000 µg, and preferably 50–500 µg muramyl dipeptide; and from about 10 to about 3000 µg, and preferably 500–2000 µg capsular polysaccharide. In a preferred regimen, animals are immunized by injection of 2 doses of the vaccine approximately 4 weeks apart. A maintenance dose is then administered on a yearly basis. As shown from the laboratory trials in the Examples below, the vaccine has been demonstrated to be effective in preventing bacterial infection of the lungs of vaccinated sheep upon challenge with *P. haemolytica*.

The following examples are intended only to further illustrate the invention and are not intended to limit the scope of the invention which is defined by the claims.

EXAMPLE 1

Vaccine Component Preparation

Capsular polysaccharide from *P. haemolytica* strain P-1075 (type A1) was prepared as described by Adlam, C., et al., *Journal of General Microbiology* 130:2415–2426, 1984. Essentially, the capsular polysaccharide was isolated from the supernatant of the initial bacterial cell harvest as follows. One liter of culture supernatant was placed in dialysis bags (12–14,500 nominal mol. wt. cutoff; Spectrum Medical Industries, Inc., Los Angeles, Calif.) and covered with carboxymethylcellulose (Aquacide I, Calbiochem Corp., La Jolla, Calif.). The concentrated culture supernatant (about 60 ml) was mixed with 3 volumes methyl alcohol and 1% sodium acetate. The resulting precipitate was pelleted by centrifugation for 30 min at 4,080×g (GSA rotor; Sorvall RC2-B centrifuge; DuPont, Wilmington, Del.) at 4° C. The supernatant was removed, filtered in a 0.22 µm filter (Nalge Co., Rochester, N.Y.) and mixed with 3 volumes of acetone. The precipitate was pelleted by centrifugation for 30 min at 4,080×g (GSA rotor; Sorvall RC2-B centrifuge; DuPont, Wilmington, Del.) at 4° C. The precipitate was resuspended in water and lyophilized. The crude acetone precipitate was dissolved in 2 volumes ¹⁄₁₀ saturated sodium acetate and 1 volume 77% (wt/vol) phenol, shaken, and centrifuged for 1 hr at 13,500×g (GSA rotor; Sorvall RC2-B centrifuge; DuPont, Wilmington, Del.) at 4° C. The aqueous phase was removed and saved. The resultant phenol phase was similarly reextracted 3 times with 2 volumes fresh, ¹⁄₁₀ saturated sodium acetate. The aqueous phases were pooled and dialyzed for 2 days against 3 changes of 0.1 M $CaCl_2$. The dialyzed aqueous phase was adjusted to pH 6.9. The mixture was then centrifuged at 100,000 ×g (Ti50 rotor; Beckman XL-90 ultracentrifuge, Beckman Instrument Co., Palo Alto, Calif.). The aqueous phase supernatant was mixed with 3 volumes ethyl alcohol with 1% sodium acetate. The precipitate was collected by centrifugation for 1 hr at 13,000×g (GSA rotor; Sorvall RC2-B; DuPont, Wilmington, Del.) at 4° C. and resuspended in 10 mM Tris, 145 mM NaCl buffer, pH 7.2 containing 0.2% SDS, and 500 µg (16 U)/ml proteinase K (Amresco, Solon, Ohio) and heated first at 60° C. for 2 hr and then overnight at 37° C. The suspension was then recycled for 1 hr over an endotoxin removing affinity column (Detoxigel; Pierce, Rockford, Ill.). The capsular polysaccharide was precipitated from the buffer with ethyl alcohol and sodium acetate. The precipitate was resuspended in pryogen-free distilled water (Baxter Healthcare Corp., Deerfield, Ill), precipitated again with ethyl alcohol and sodium acetate, resuspended in pryogen-free distilled water and lyophilized. The capsular polysaccharide contained less than 0.25% protein [Bradford, M. M., "A rapid and sensitive method for the quantitation of microgram quantities of protein utilizing the principle of protein-dye binding," Analytical Biochemistry 72:248–254 (1976)] and 0.01% LPS as determined by a chromogenic limulus amebocyte lysate assay (QCL-1000, Whittaker Bioproducts, Walkersville, Md.).

Muramyl dipeptide (N-acetylmuramyl-L-alanyl-D-isoglutamine) was chemically synthesized.

Vaccine Formulation

Separate stock solutions of capsular polysaccharide (2 mg/ml) and muramyl dipeptide (1.25 mg/ml) were prepared in 0.14 M NaCl containing 0.2% sorbitan monooleate and 0.1% formalin and chilled on ice. Vaccine 1 was formulated from 2.75 ml of capsular polysaccharide solution, 0.22 ml of muramyl dipeptide solution, 6.93 ml of a mixture of 0.2% sorbitan monooleate and 0.1% formalin, and 1.1 ml of mineral oil. Vaccine 2 was formulated from 2.75 ml of capsular polysaccharide solution and 7.10 ml of a mixture of 0.2% sorbitan monooleate and 0.1% formalin, and 1.1 ml of mineral oil. All vaccines were emulsified in the sonicator for 60 sec. Final concentrations were 0.5 mg capsular polysaccharide/ml and 25 µg muramyl dipeptide/ml of vaccine.

Lamb Field Trial

Fifteen, 11-to 14-week-old (12.7+1.4 weeks) Columbia lambs of both sexes were used. Lambs were collected at birth, deprived of colostrum, and housed in isolation. The lambs were assigned into 3 groups. Two groups of lambs (n=5 lambs each) were inoculated intramuscularly at days 0 and 28 with 2 ml of vaccines 1 and 2, respectively. A third group of lambs (n=5 lambs) was not inoculated and served as challenge exposure controls. On day 42, all lambs were inoculated with tissue culture media containing ovine adenovirus strain OAV-6. The inoculum was injected intratracheally (2 ml tissue culture medium containing virus) and dispensed intranasally (1 ml tissue culture medium containing virus in each nostril). On day 46, lambs were inoculated intratracheally with 106 ml tryptose broth containing $4.5 \times 10^6$ CFU *P. haemolytica*/ml.

On day 71, lambs were anesthetized with pentobarbital and exsanguinated. At necropsy, lesions were seen in the lungs of all lambs due to the underlying adenovirus challenge. However, lesions observed due the secondary *P. haemolytica* challenge varied among groups as reported in Table I, below.

TABLE I

Extent of Pneumonia in Lungs of Lambs after Vaccination
(Average percent pulmonary consolidation)

| Pulmonary lobe | Non-vaccinated | Vaccine 1 (CP + MDP) | Vaccine 2 (CP) |
| --- | --- | --- | --- |
| right anterior | 41 | 11 | 26 |
| middle | 40 | 19 | 33 |
| diaphramic | 2 | 2 | 1 |
| left anterior | 22 | 14 | 23 |
| middle | 41 | 30 | 50 |
| diaphramic | 7 | 5 | 7 |
| accessory | 30 | 10 | 31 |

Lungs were homogenized and the concentration of viable organisms was determined. The concentrations of *P. haemolytica* isolated from these lesions also varied among groups as shown in Table II, below.

TABLE II

Concentration of *P. haemolytica* in the Lungs
After Experimental Challenge

| Vaccine | Lesions[a] | Isolation[b] | Concentration[c] |
| --- | --- | --- | --- |
| none | B, V | 5/5 | $2.4 \times 10^7$ |
| vaccine 1 (CP + MDP)[d] | V | 0/5 | 0 |
| vaccine 2 (CP) | B, V | 4/5 | $3.7 \times 10^7$ |

[a]Primarily bacterial (B) or viral (V) lesions.
[b]Number positive/total number in group.
[c]Concentration per gram of lung tissue.
[d]CP = capsular polysaccharide and MDP = muramyl dipeptide.

EXAMPLE 2

Vaccines 1 and 2 were formulated as described in Example 1. Fifteen specific pathogen-free Columbia lambs of both sexes were used in the trial. The average age of the lambs at the start of the study was 62 days (range 56–70 days) and the mean body weight was 27 kg (range 22–32 kg). The lambs were assigned into 3 vaccine groups. Groups receiving vaccines 1 and 2 (n=5 lambs each) were inoculated intramuscularly in the right rear leg at days 0 and 28 with 2.0 ml of vaccine. A third group (n=5 lambs) was not inoculated and served as challenge exposure controls. Vaccination sites were examined weekly and palpitated for the presence of swelling. On day 34, lambs were inoculated with tissue culture media containing ovine adenovirus strain OAV-6. The inoculum was injected intratracheally (2 ml tissue culture medium containing virus) and dispensed intranasally (1 ml tissue culture medium containing virus in each nostril). On day 38, lambs were inoculated intratracheally with 10 ml tryptose broth containing $5.7 \times 10^6$ CFU *P. haemolytica*/ml.

Buprenx (0.005 mg/kg) was administered subcutaneously every 12 hours to sheep with respiratory difficulty.

On day 40, lambs were anesthetized with sodium pentobarbital (1.3 gm) and exsanguinated. At necropsy, the lungs were evaluated macroscopically for bacterial and viral lesions and the vaccination site was examined for tissue damage. Pieces of the right middle lobe were taken for quantitative bacterial culture and pieces of the right middle lobe and intramuscular injection site were taken for histopathologic examination. Duplicate pieces of the right middle lobe of the lung from each lamb were diced and homogenized in 100 ml of tryptose broth. The homogenate was diluted in tryptose broth, plated on trypticase soy agar with 5% defibrinated sheep blood, and the plates were incubated for 24 hours at 37° C. Pieces of lung were fixed in 10% neutral buffered formalin solution, embedded in paraffin, sectioned, and stained with Giemsa and hematoxylin and eosin stains.

Small, pea-sized nodules were felt at the vaccination site in ⅖ lambs that received vaccine 1, and in ⅗ lambs that received vaccine 2.

Nodules could not be felt on any lamb by day 21. At necropsy, lesions were seen in the lungs of all lambs due to the underlying adenovirus challenge. However, lesions associated with the secondary *P. haemolytica* challenge varied among groups and were restricted primarily to the middle lobes of both the right and left lungs as shown in Table III, below.

TABLE III

Extent of Pneumonia in Lungs of Lambs after Vaccination
(Average percent pulmonary consolidation)

| Pulmonary lobe | Non-vaccinated | Vaccine 1 (CP + MDP)[a] | Vaccine 2 (CP) |
|---|---|---|---|
| right anterior | 13 | 14 | 8 |
| middle | 31 | 21 | 26 |
| diaphramic | 0 | 1 | 0 |
| left anterior | 8 | 4 | 10 |
| middle | 25 | 4 | 30 |
| diaphramic | 8 | 3 | 2 |
| accessory | 6 | 7 | 7 |

[a]CP = capsular polysaccharide and MDP = muramyl dipeptide.

Overall, all lambs had histologic evidence of viral pneumonia characterized by type II pneumocyte hyperplasia and both peribronchiolar and perivascular lymphocyte cuffs. Some lambs had histologic evidence of bacterial pneumonia that varied among vaccination groups.

In the nonvaccinated controls, 4/5 had evidence of bacterial pneumonia characterized by hemorrhage, fibrin, inflammatory cell infiltrates, and bacteria. In lambs vaccinated with capsular polysaccharide and muramyl dipeptide, there were minimal lesions attributed to bacterial infection. Low numbers of inflammatory cell infiltrates and small amount of hemorrhage were seen.

All 5 lambs vaccinated with capsular polysaccharide had lesions characteristic of bacterial pneumonia described above. One of these lambs had lesions probably the severest of the study.

The concentrations of P. haemolytica isolated from these lesions appeared to correlate with the gross and histopathologic observations as shown in Table IV, below.

TABLE IV

Concentration of P. haemolytica in the Lungs
After Experimental Challenge

| Vaccine | Lesions[a] | Isolation[b] | Range[c] | Concentration[d] |
|---|---|---|---|---|
| none | B, V | 4/5 | $2.7 \times 10^1$–$8.4 \times 10^5$ | $2.8 \times 10^5$ |
| Vaccine 1 (CP + MDP)[e] | V | 3/5 | $0.2$–$3.6 \times 10^2$ | $9.9 \times 10^1$ |
| Vaccine 2 (CP) | B, V | 5/5 | $5.5 \times 10^0$–$1.7 \times 10^7$ | $3.4 \times 10^6$ |

[a]Primarily bacterial (B) or viral (V) lesions.
[b]Number of lambs with P. haemolytica/total lambs in group.
[c]Range of concentration of P. haemolytica in the infected lungs.
[d]Mean concentration of P. haemolytica per gram of infected lung tissue.
[e]CP = capsular polysacharide and MDP = muramyl dipeptide.

EXAMPLE 3

The procedure of Example 2 was repeated using the same capsular polysaccharide vaccine control and nonvaccinated control groups to illustrate the efficacy of a capsular polysaccharide +muramyl dipeptide glyceryl dipalmitoyl vaccine. Capsular polysaccharide from P. haemolytica strain P-1075 (type A1) was prepared as described in Example 1. Muramyl dipeptide glyceryl dipalmitoyl is the chemically synthesized derivative of the N-acetylmuramyl-L-alanyl-D-isoglutamine of Example 1. The vaccines were formulated exactly as described in Example 1 except muramyl dipeptide glyceryl dipalmitoyl was substituted for the muramyl dipeptide.

Five specific pathogen-free Columbia lambs of both sexes were selected, vaccinated, and then exposed on day 34 to ovine adenovirus strain OAV-6 and on day 38 to $5.7 \times 10^6$ CFU P. haemolytica/ml as described in Example 2. At necropsy on day 40, the lungs were evaluated for bacterial and viral lesions and the vaccination site was examined for tissue damage and pieces were taken for histopathologic examination. Pieces of the right middle lobe were also taken for quantitative bacterial culture as described in Example 1.

Small, pea sized nodules were felt at the vaccination site in 5/5 lambs that received this vaccine. Nodules could not be felt on any lamb by day 21. This lesion was characterized by multiple granulomas with lipid laden macrophages, degeneration and mineralization of myocytes, and fibrosis.

At necropsy, lesions were seen in the lungs of all 5 lambs due to the underlying adenovirus challenge. However, lesions associated with the secondary P. haemolytica challenge varied among lambs and were restricted primarily to the middle lobes of both the right and left lungs as shown in Table V, below.

TABLE V

Extent of Pneumonia in Lungs of Lambs after Vaccination
(Average percent pulmonary consolidation)

| | Non-vaccinated | CP + MDP-GDP vaccine[a] | CP vaccine |
|---|---|---|---|
| right anterior | 13 | 9 | 8 |
| middle | 31 | 19 | 26 |
| diaphragmic | 0 | 1 | 0 |
| left anterior | 8 | 1 | 10 |
| middle | 25 | 11 | 30 |
| diaphragmic | 8 | 1 | 2 |
| accessory | 6 | 6 | 7 |

[a]CP = capsular polysaccharide and MDP-GDP = muramyl dipeptide glyceryl dipalmitoyl.

Overall, 1 lamb had severe areas and 2 lambs had mild areas of bacterial pneumonia characterized with pleuritis, degenerating alveolar macrophages, inflammatory cell infiltrates, fibrin and hemorrhage. The remaining 2 lambs in this group did not have evidence of bacterial pneumonia.

The concentrations of P. haemolytica isolated from these lesions correlated with the gross and histopathologic observations as shown in Table VI, below.

TABLE VI

Concentration of P. haemolytica in the lungs
After Experimental Challenge

| Vaccine | lesions[a] | isolation[b] | range[c] | concentration[d] |
|---|---|---|---|---|
| none | B, V | 4/5 | $2.7 \times 10^1$–$8.4 \times 10^5$ | $2.8 \times 10^5$ |
| CP + MDP-GDP[e] vaccine | V | 3/5 | $9.2 \times 10^0$–$1.4 \times 10^4$ | $5.2 \times 10^3$ |
| CP vaccine | B, V | 5/5 | $5.5 \times 10^0$–$1.7 \times 10^7$ | $3.4 \times 10^6$ |

[a]Primarily bacterial (B) or viral (V) lesions.
[b]Number of lambs with P. haemolytica /total lambs in group.
[c]Range of concentration of P. haemolytica in the infected lungs.
[d]Mean concentration of P. haemolytica per gram of infected lung tissue.
[e]CP = capsular polysaccharide and MDP-GDP = muramyl dipeptide glyceryl dipalmitoyl.

It is understood that the foregoing detailed description in the examples is given merely by way of illustration and that modification and variations may be made therein without departing from the spirit and scope of the invention.

We claim:

1. A vaccine composition comprising *Pasteurella haemolytica* capsular polysaccharide and muramyl dipeptide in pharmaceutically acceptable carrier or vehicle.

2. The composition of claim 1 wherein said muramyl dipeptide is represented by the general formula:

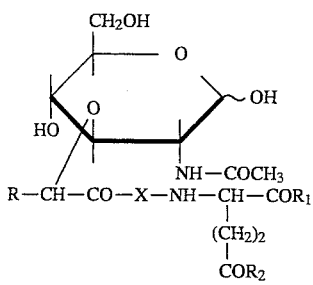

where

R is a hydrogen or a methyl group.

X is an amino acid.

R1 is OH, $NH_2$ or $OCnH_{2+1}$ with n being 1, 2, 3 or 4.

R2 is OH, NH2, $OC_nH_{2n+1}$ (with n being up to 20), sn glyceryl dipalmitoyl or Y-Z.

Where Y is an amino acid and Z is OH, $NH_2$, $OCnH_{2n+1}$ with n being up to 20 or sn glyceryl dipalmitoyl.

3. The composition of claim 1 wherein said muramyl dipeptide is selected from the group consisting of N-acetyl-muramyl-L-alanyl-D-isoglutamine and N-acetyl-muramyl-L-alanyl-D-isoglutamine, beta, gamma-dipalmitoyl-sn-glycerol.

4. The composition of claim 1 wherein said capsular polysaccharide comprises N-acetylaminomannuronic acid and N-acetylmannosamine.

5. The composition of claim 1 further comprising an oleagenous carrier and an emusifying agent.

6. A method for protecting a ruminant animal from stress-induced virulence of *Pasteurella haemolytica* comprising administering to the animal a a vaccine composition comprising *P. haemolytica* capsular polysaccharide and muramyl dipeptide in pharmaceutically acceptable carrier or vehicle.

7. The method of claim 6 wherein said muramyl dipeptide is represented by the general formula:

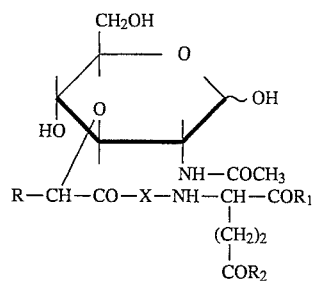

where

R is a hydrogen or a methyl group.

X is an amino acid.

R1 is OH, $NH_2$ or $OCnH_{2n+1}$ with n being 1, 2, 3 or 4.

R2 is OH, NH2, $OC_nH_{2n+1}$ (with n being up to 20), sn glyceryl dipalmitoyl or Y-Z.

Where Y is an amino acid and Z is OH, $NH_2$, $OCnH_{2n+1}$ with n being up to 20 or sn glyceryl dipalmitoyl.

8. The method claim 6 wherein said muramyl dipeptide is selected from the group consisting of N-acetylmuramyl-L-alanyl-D-isoglutamine and N-acetyl-muramyl-L-alanyl-D-isoglutamine, beta, gamma-dipalmitoyl-sn-glycerol.

9. The method of claim 6 wherein said capsular polysaccharide comprises N-acetylaminomannuronic acid and N-acetylmannosamine.

10. The method of claim 6 wherein said composition further comprises an oleagenous carrier and an emusifying agent.

11. The method of claim 6 wherein said animal is a sheep.

12. The method of claim 6 wherein said animal is a bovine.

13. The composition of claim 2 wherein X is an amino acid selected from the group consisting of L-Ala, L-Leu, L-ILeu, L-Val, L-Ser, L-Thr, L-(N-Methyl) Ala, and D-Ala.

14. The composition of claim 2 wherein Y is an amino acid selected from the group consisting of L-Ala or L-Lys.

15. The method of claim 7 wherein X is an amino acid selected from the group consisting of L-Ala, L-Leu, L-ILeu, L-Val, L-Ser, L-Thr, L-(N-Methyl) Ala, and D-Ala.

16. The method of claim 7 wherein Y is an amino acid selected from the group consisting of L-Ala or L-Lys.

* * * * *